United States Patent [19]

Bigner et al.

[11] Patent Number: 5,316,932
[45] Date of Patent: May 31, 1994

[54] HOMOGENEOUS DENATURED HUMAN O6-GUANINE ALKYLTRANSFERASE PREPARED BY IMMUNOAFFINITY CHROMATOGRAPHY USING MONOCLONAL ANTIBODY SPECIFIC FOR ENZYME

[75] Inventors: Darell D. Bigner, Chapel Hill, N.C.; Thomas P. Brent, Memphis, Tenn.

[73] Assignees: Duke University, Durham, N.C.; St. Jude Children's Research Hospital, Memphis, Tenn.

[21] Appl. No.: 59,414

[22] Filed: May 11, 1993

Related U.S. Application Data

[63] Continuation of Ser. No. 799,877, Nov. 27, 1991, abandoned, which is a continuation of Ser. No. 703,700, May 21, 1991, abandoned, which is a continuation of Ser. No. 328,504, Mar. 24, 1989, abandoned.

[51] Int. Cl.$^5$ .......................... C12N 9/10; C07K 3/00
[52] U.S. Cl. .................................... 435/193; 435/803; 435/814; 530/413
[58] Field of Search ...................... 435/193, 803, 814; 530/413

[56] References Cited

U.S. PATENT DOCUMENTS

| | | | |
|---|---|---|---|
| 4,123,427 | 10/1978 | Daniel | 530/413 |
| 4,474,893 | 10/1984 | Reading | 530/413 |
| 4,789,631 | 12/1988 | Maggio | 530/413 |
| 4,789,734 | 12/1988 | Pierschbacher | 530/413 |
| 5,136,027 | 8/1992 | Pope | 530/427 |
| 5,158,875 | 10/1992 | Miller et al. | 435/69.1 |
| 5,162,507 | 11/1992 | Wolfe et al. | 530/412 |
| 5,175,104 | 12/1992 | Asahi et al. | 435/194 |
| 5,187,080 | 2/1993 | Andrews e tal. | 435/69.3 |
| 5,187,153 | 2/1993 | Cordell et al. | 514/12 |
| 5,191,063 | 3/1993 | Inouye et al. | 530/324 |

OTHER PUBLICATIONS

Harris et al., Cancer Research, vol. 43, 3247–3252, 1983.
Dolan et al., Carcinogenesis (London), 9 (11), Sequence Specificity of Guanine . . . , pp. 2139–2143, 1988.
Wiestler et al., Carcinogenesis (London), 5 (1), O$^6$-Alkylguanine–DNA alkytransferase . . . , pp. 121–124, 1984.
Hall et al., Carcinogenesis (London), 6 (2), O$^6$-Alkylguanine–DNA alkyltransferase . . . , 207–211, 1985.
Grafstrom et al., Cancer Research, 44, O$^6$-Alkylguanine–DNA Alkyltransferase Acitivity . . . , pp. 2855–2857, 1984.
Geysen et al., Science, vol. 235, Mar. 6, 1987, pp. 1184–1190.
Sharma et al., Proc. Nat'l. Acad. Sci. U.S.A., vol. 77, No. 10, pp. 5865–5868, 1980.
Jones, Amer. J. Physiol. S2: 203–207, 1920.
Sela et al., Biochima FT Biophysica, Act A, 26:S02–512, 1957.

Primary Examiner—David M. Naff
Assistant Examiner—Michael V. Meller
Attorney, Agent, or Firm—Cushman, Darby & Cushman

[57] ABSTRACT

A denatured human O$^6$-guanine alkyltransferase is disclosed. The enzyme is prepared by a process which involves denaturing the enzyme, contacting the denatured enzyme with a monoclonal antibody specific for the denatured enzyme on a substrate to which the monoclonal antibody is bound to, so that the denatured enzyme and the monoclonal antibody form an immunocomplex and then, eluting the denatured enzyme from the substrate-bound monoclonal antibody so that the denatured human O$^6$-guanine alkyltransferase is obtained. The enzyme can be used to develop probes for the Mer$^-$ phenotype and these probes in turn are contemplated for use in identifying drug resistant tumors in patients.

4 Claims, 4 Drawing Sheets

HOMOGENEOUS DENATURED HUMAN O6-GUANINE ALKYLTRANSFERASE PREPARED BY IMMUNOAFFINITY CHROMATOGRAPHY USING MONOCLONAL ANTIBODY SPECIFIC FOR ENZYME

Portions of the work contained herein were supported by Grants CA 14799, CA 36888, CA 21765, CA 11898 and NS 20023 from the NIH and by ALSAC.

This is a continuation of application Ser. No. 07/799,877, filed on Nov. 27, 1991, which was abandoned upon the filing hereof, which is a continuation of application Ser. No. 07/703,700, filed May 21, 1991, now abandoned, which is a continuation of application Ser. No. 07/328,504, filed Mar. 24, 1989, now abandoned.

FIELD OF THE INVENTION

The present invention relates to the production of monoclonal antibodies specific for human $O^6$-guanine alkyltransferase, and the use of such MAbs in an immunopurification process which permits the recovery of a homogenous protein product.

BACKGROUND OF THE INVENTION

Human $O^6$-guanine alkyltransferase ("GATase") is a suicide enzyme that irreversibly transfers an alkyl adduct from the $O^6$-position of guanine onto a cysteine residue in its active site. $O^6$-alkylguanine-DNA alkyltransferase is responsible for the repair of mutagenic lesions induced by simple methylating agents, as well as for the repair of precursors of cytotoxic interstrand cross-links which are induced by chloroethylating anticancer drugs. The enzyme is of growing interest in cancer chemotherapy research because of its ability to suppress formation in vitro of chlorethylnitrosourea (CENU)-induced DNA interstrand cross-links, which are considered to be the cytotoxic lesions generated by these agents. Consistent with these observations, the susceptibility of human cancer cell lines and human tumor xenografts to CENU therapy correlates with their levels of GATase activity.

About 20% of cultured human tumor cell lines, termed Mer[31], appear deficient in GATase activity and are hypersensitive to the lethal effects of CENUs and agents that induce $O^6$-methylguanine in DNA. By contrast, cells derived from normal tissues do not display such hypersensitivity, suggesting the opportunity for selective therapy for patients with the Mer− (methyl repair minus) subset of tumors.

The presence of Mer− tumors in patients remains to be established. Wiestler et al. (Carcinogenesis 15:121-124(1984)) found in a series of 23 human tumor biopsy specimens, that all contained measurable $O^6$-guanine alkyltransferase activity. This failure to identify Mer− tumors could, however, merely reflect contamination of the specimens by normal host stroma cells, or it may indicate that the Mer− phenotype is not a property of human tumors in situ, but arises during adaptation to tissue culture or the establishment of xenografts.

Resolution of these questions requires both sequence and structural analysis of the $O^6$-guanine alkyltransferase, studies which have been greatly impaired, if not entirely prohibited, by the inability to purify the GATase protein to homogeniety. Additionally, conventional methods have, to date, proved unsuccessful in raising monoclonal antibodies ("MAbs") to the subject protein, thus further restricting the use of and research relating to the human GATase enzyme.

SUMMARY OF INVENTION

The present application is directed to a method for raising monoclonal antibodies against the human $O^6$-guanine alkyltransferase enzyme, and the use of these antibodies in the immunopurification of the GATase protein; the disclosed process resulting in a purified, homogeneous enzyme.

The present invention is advantageous over the state of the art, for it achieves a highly purified GATase protein which is required for sequence and structural analysis. It is contemplated that ability to achieve a highly pure protein will enable those skilled in the art to the develop probes for the Mer− phenotype, and these probes in turn are contemplated for use in identifying drug resistant tumors in patients.

Prior to the present invention, no one had achieved purification of the human $O^6$-guanine alkyltransferase to homogeniety. While GATase had been partially purified by various methods and to various extents (see e.g., Brent, Pharmac. Ther. 31:121-140 (1985)), in no case did the purification achieve a homogenous product. For example, by means other than those disclosed herein, we have purified the transferase 500-fold to achieve a specific activity of 800 pmoles/mg protein. This value is, however, at least 50-fold short of the specific activity calculated for homogeneous GATase (40,000 pmoles/mg protein) on the basis of the 25,000 dalton molecular weight of the protein.

In addition to the above, prior to the present invention, no one had been successful in producing MAbs to the GATase protein. In fact, the only reference to date which describes the production of antibodies to GATase is a preliminary report by Yarosh and Ceccoli (Proc. Am. Assoc. Can. Res. 29:(1) (1988)) which discloses mouse antiserum raised against partially purified GATase from human liver.

In order to obtain the homogeneous (approximately 30,000-fold purified) protein of the present invention, we have produced four stable hybridomas that secrete monoclonal antibodies against the alkyltransferase from human lymphoblasts. The specificity of these monoclonals has been established by immunoblot analysis and immunoprecipitation, and representative MAbs designated 19.2 and 4.A1 have been used successfully in immunoaffinity chromatography to achieve the highly purified transferase of the present invention.

Thus, this application for the first time discloses and describes GATase specific monoclonal antibodies, the use of such antibodies to immunopurify the GATase enzyme, and the homogeneous product achieved thereby.

The invention will be more fully described below by the drawings and in the detailed description of the invention. The invention should in no way be limited by these drawings and examples which serve only to disclose a preferred embodiment of the invention; modifications to which will be readily apparent to those skilled in the art and are therefore contemplated to fall within the scope of the present invention.

DETAILED DESCRIPTION OF THE INVENTION

Figure 1:
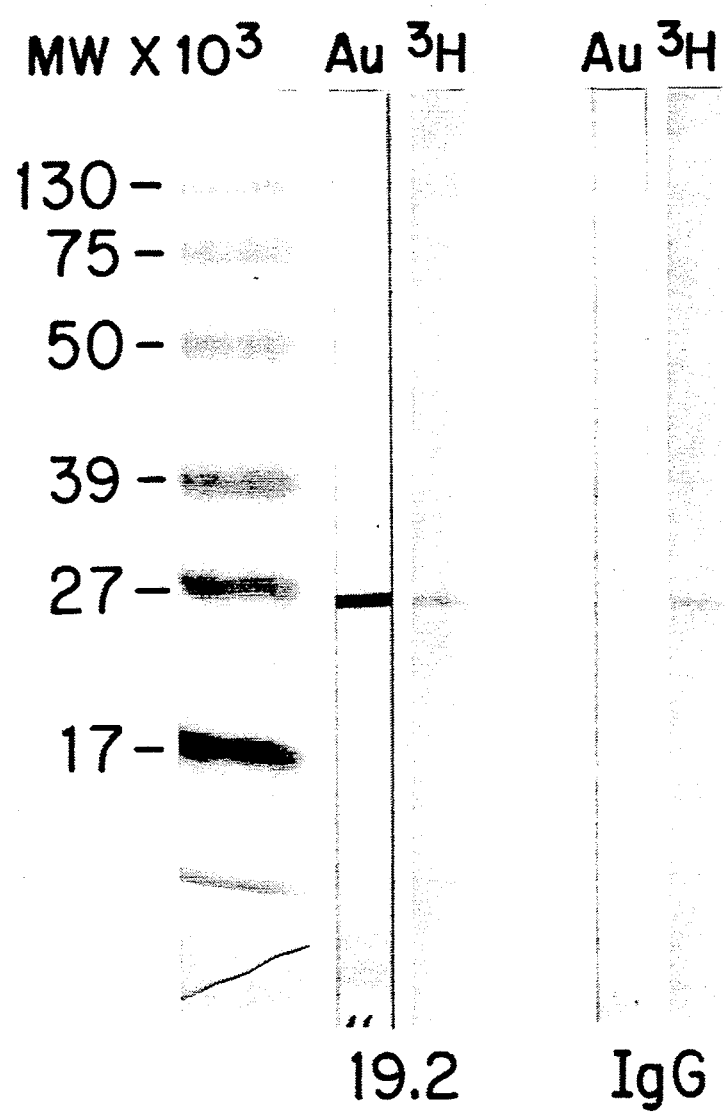
FIG. 1. Immunoblot of $^3$H-labeled GATase (Fraction 3). Pre-stained molecular weight markers (Bio-Rad—Richmond, Calif.) are shown on the left. Strips of the blot from PAGE, probed with MAb 19.2 or non-immune IgG, followed by gold labeled secondary antibody are labeled "Au". The corresponding autoradiographs (labeled, "$^3$H") are shown to the right of each blot.

All references cited herein are to be specifically incorporated into the application by reference.

A. Cell Culture

Human leukemic lymphoblasts (CEM-CCRF line) (Thomas Brent, St. Jude Children's Hospital, Memphis, Tenn.) were grown in suspension in roller bottles as described by Brent, Pharmac. Ther. 31:121-140 (1985). Human rhabdomyosarcoma lines Rh18 (Mer+) and Rh28 (Mer−) (Peter Houghton, St. Jude Children's Hospital, Memphis, Tenn.) were grown as monolayers as described by Smith and Brent, Cancer Res. 49:883-886 (1989). Human medulloblastoma cell line TE-671 (Mer+) (Robert McAllister, Children's Hospital, Los Angeles, Calif.) and human glioma cell line D54-MG (Mer−) (Darell Bigner, Duke University, Durham, N.C.) were grown as described by McAllister et al. (Int. J. Cancer 20:206-212 (1977)), Wikstrand et al. (Cancer Res. 43:3327-3334 (1983)), and Bigner et al. (J. Neuropath. Exp. Neurol. 40:201-239 (1981)).

B. Preparation of GATase for Immunization

About 120 pmoles of 10-fold purified GATase (Fraction 3, Ref 9) from cultured human lymphoblasts (CEM-CCRF line) were labeled by reaction with [$^3$H]MNU-treated DNA as described by Brent, supra. A 10-fold purified protein preparation was selected for use in order to ensure the production of adequate amounts of the immunogen for use in the disclosed studies. Both 10- and 500-fold purified preparations have been employed in the past. Both preparations contain multiple human protein bands in addition to GATase on SDS-PAGE, and neither are sufficiently pure to sequence or to use in structural analysis, etc.

The protein labeled above was further purified by electrophoresis on 10% polyacrylamide SDS gels according to the method of Laemmli (Nature 227:680-685 (1970)), using a Protean II slab gel apparatus (Bio-Rad, Richmond, Calif.). The gels were then cut into 5-mm horizontal bands, and radioactivity was determined in narrow strips at the edges and center by liquid scintillation counting to identify the 25-KDa band containing the $^3$H-labeled GATase.

The polyacrylamide gel band containing about 3 μg GATase was homogenized in 3 ml of 115 mM phosphate buffer (pH 7.4) with a Brinkman Polytron homogenizer, and then emulsified with an equal volume of complete Freund's adjuvant (Difco Laboratory, Detroit, Mich.). This preparation of the immunogen was used for subcutaneous injections.

For intravenous injection, [$^3$H-methyl]-labeled GATase was electroeluted from the 25-KDa band in the gel using an Isco sample concentrator (Model 1750), essentially as described by Brown et al. (Anal. Biochem. 103:184-190 (1980)). Protein eluted from the gel was concentrated in buffer containing 3.75 mM Tris-HCl (pH 8.8) and 2 mM EDTA using Spectropore dialysis membrane with a 12-KDa cutoff. The amount of [$^3$H-methyl]-labeled GATase recovered was calculated from the specific activity of the [$^3$H-methyl]-radiolabel.

C. Hybridoma Formation

Each of three female Balb/C mice were injected subcutaneously at several sites with the homogenized polyacrylamide gel slices containing purified GATase (about 1 μg/mouse). The mice were boosted subcutaneously with about 1 μg GATase in homogenized gel slices on days 29, 51, 85, 120 and 190 after primary immunization. Blood collected from the mice on day 7 and day 14 after each injection of GATase was tested by immunofluorescence for serum antibody titers against two Mer+ cell lines, Rh18 and TE671, relative to two Mer− cell lines, Rh28 and D54MG.

After the fifth subcutaneous boost, the mice were rested for 136 days and then injected intravenously on 3 consecutive days with about 1 μg of GATase that had been electroeluted from the polyacrylamide gel band. On the fourth day, spleens were removed from two of the mice that had shown a marked differential antibody response against the Mer+ cell lines. The spleen cells from these mice were fused with the Kearney variant myeloma designated P3.X63.Ag8.653 (ATCC, Rockville, Md.—Accession No. CRL1580) as described by Kerney et al. in J. Immunol. 123:1548-1550 (1979).

D. Immunofluorescence Assay for Anti-GATase Antibodies

Mer+ and Mer− cell lines were plated on 9×9 mm coverslips. When cells were 60% to 80% confluent, coverslips were fixed in cold acetone (−20° C.) for 60 seconds.

Fixed coverslips were blocked for 1 hour with 10% normal goat serum (Life Technologies Inc., Gaithersburg, Md.) in 115 mM phosphate buffer (pH 7.4), then covered with primary antibody from several of the hybridomas and incubated overnight at 4° C. After rinsing, the coverslips were covered with 1 μg/ml biotinylated goat anti-mouse IgG (BRL, Bethesda, Md.—cat. no. 9588SA) in 10% normal goat serum and incubated for 1 hour at room temperature. The plates were then rinsed, covered with streptavidin-FITC (BRL cat. no. 9538SA), and incubated for an additional hour at room temperature, after which time they were rinsed again and mounted in 75% glycerol and 25% 115 mM phosphate buffer (pH 7.4). The coverslips were examined with a Zeiss Universal Fluorescence microscope with epiillumination and scored on a scale from negative to 4 plus.

As noted above, initial screening for anti-GATase antibody secreting hybridomas was against Mer+ cell lines, Rh-18 and TE-671. Eighty-one hybridomas that were scored positive with the Mer+ cell lines were further screened in a solid-phase ELISA assay against GATase prepared by electroelution from PAGE gel bands. Thirty-seven hybridomas that reacted with the electroeluted GATase were selected for cloning by limiting dilution in Methocel (Wilkstrand and Bigner, Cancer Research 42:267-275 (1982)).

Cloned hybridoma immunoglobulin subclass types were determined from tissue culture supernatants by immunodiffusion using a subclass typing kit (Miles Laboratories, Elkhart, Ind.—Product No. 64-690-1).

E. ELISA Assay for Monoclonal Antibodies

Two variations of ELISA (Enzyme Linked ImmunoSorbent Assay) were used. In the first method, Mer+ cells were plated into 96 well tissue culture plates (Flow Laboratories, McLean, Va.—cat. no. 76-032-05) at a concentration of $2.5 \times 10^4$ to $1 \times 10^5$ per well and incubated at 37° C. until there was a confluent monolayer. The plates were then rinsed with Dulbecco's phosphate-buffered saline (DPBS) (Grand Island Biological, Grand Island, N.Y.) and fixed with 0.25% BM grade glutaraldehyde (Sigma Chemical Colo., St. Louis, Mo.) in DPBS for 60 seconds, before being fixed for 2 minutes with 95% cold (−20° C.) ethanol.

In the second ELISA method, 1 μg of electroeluted GATase was diluted in 10 ml of 0.1M sodium bicarbonate buffer (pH 9.6), and 50 μl was added per well to a 96 well ELISA plate (Dyantech Laboratories, Chantilly, Va.—cat. no. 001-010-2801).

In both methods, the plates were then blocked with 10% normal goat serum for 1 hour at room temperature. Subsequently, 50 μl of hybridoma culture supernatant or control myeloma supernatant was added to triplicate wells and the plates were incubated overnight at 4° C. Each well was rinsed five times and 50 μl of 1 μg/ml biotinylated goat anti-mouse (BRL cat. no. 9588SA) in 10% normal goat serum was added per well and incubated for 1 hour at room temperature. After rinsing five times, the plates were incubated for 1 additional hour with 50 μl per well of streptavidin-alkaline phosphatase (BRL cat. no. 9542SA), and rinsed five times more before color development with an ELISA amplification kit (BRL cat no. 9589SA). Optical densities of wells were read with a Flow Laboratories ELISA plate reader model MCC/340. Binding ratios were calculated by the formula:

$$\frac{O.D. \text{ Hybridoma Supernatant}}{O.D. \text{ Control Myeloma Supernatant}}$$

Hybridomas with a binding ratio of two or greater against the Mer+ cell lines were retained for further study.

F. Purification of Monoclonal Antibodies

Supernatant or ascites was diluted with an equal volume of 3M NaCl and 1.5M glycine buffer (pH 8.9) and filtered through a 0.22 micron Millistak filter (Millipore Corp., Bedford, Mass.—cat. no. SLGV025LS). The culture supernatant or ascites was then passed over a 15×2.5 cm protein-A column (7.5 g Staph A:Sepharose 4B, (Sigma Chem. Co. —cat. no. P3391)), and the column rinsed with 10 to 15 column volumes of 1.5M NaCl and 0.75M glycine buffer (pH 8.9). The column was then eluted with 0.55M glycine buffer (pH 3.5) containing 0.85% NaCl. The resulting fractions were immediately neutralized by the addition of 1M Tris buffer (pH 9.0), and those fractions containing antibody were pooled and dialyzed against 0.115M phosphate buffer (pH 7.4).

The protein concentration of antibody was determined by the Lowry method (Lowry et al., Biol. Chem. 193:265–275 (1951)) and the antibody was sterilized by passing it through a 0.22 micron Millipore Millex-GV filter and stored at either 4° C. or at −70° C.

Monoclonal antibodies from the cloned hybridomas were purified and further characterized by Western blot analysis.

G. Western Blotting $^3$H-methyl]-labeled GATase (Fraction 3, 50 μg total protein per lane) was separated on a 12.5% SDS-polyacrylamide gel by the method of Laemmli, supra, and transferred to nitrocellulose (Schleicher and Schuell, Keene, NH; BA83) for 2 hours at 60V essentially according to the method of Towbin et al. (Proc. Natl. Acad. Sci. USA 76:4350–4354 (1979)) using a Bio-Rad mini-gel apparatus.

The blot was blocked with 5% BSA (Bovine Serum Albumen (Janssen, Piscataway, N.J.) and cut into strips which were probed with either MAb or non-immune mouse myeloma IgG$_1$, 10 μg/ml in a buffer (Buffer A) containing 20 mM Tris-HCl (pH 8.2), 0.1% BSA, 0.9% NaCl and 1% normal goat serum (Gibco, Grand Island, N.Y.). Visualization of antibody binding was carried out using Janssen's gold-labeled goat anti-mouse IgG secondary antibody and silver enhancement kit (Janssen, Piscataway, N.J.) according to the manufacturer's instructions.

Figure 2:
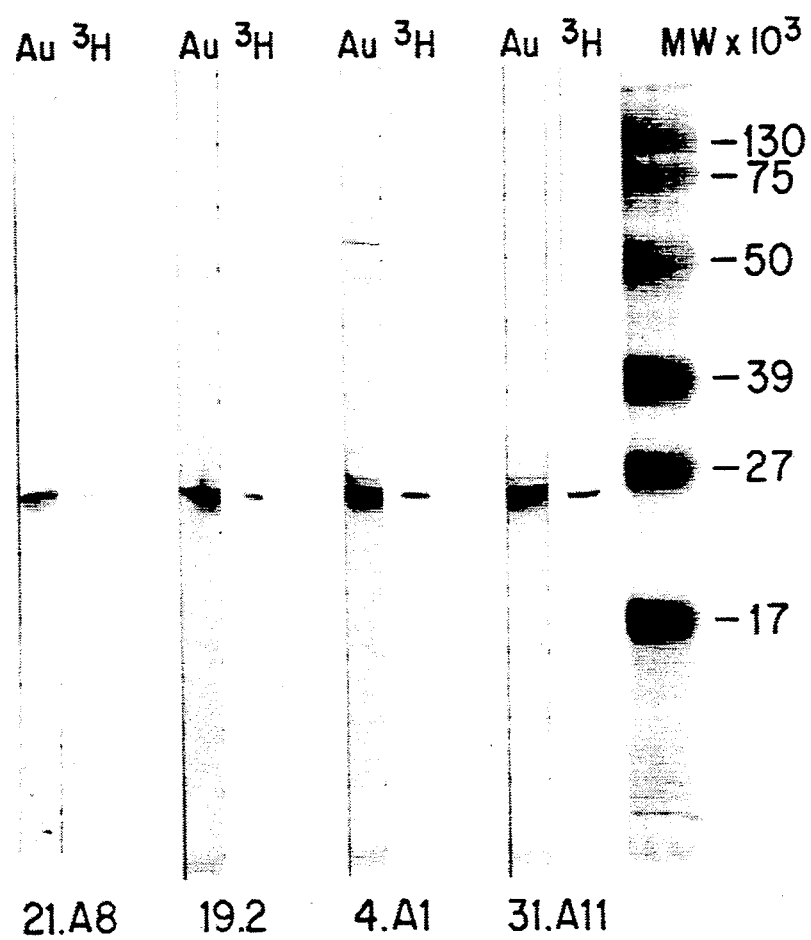
FIG. 2. Immunoblot of $^3$H-labeled GATase (Fraction 3) probed with MAbs 4.A1, 21.A8, and 31.A11; MAb 19.2 is shown for comparison. Immunoprobed strips and their autoradiographs are labeled "Au" and "$^3$H" as in FIG. 1.

One of the monoclonals, designated 19.2, recognized a single protein band migrating at 25-kDa (FIG. 1). The autoradiograph of this blot demonstrated that the immunoreactive band coincided with the position of the $^3$H-labeled GATase (FIG. 1). A duplicate control strip probed with non-immune IgG showed no reaction, although its autoradiograph confirmed that [$^3$H-methyl]-labeled GATase was present at 25-kDa. FIG. 2 shows immunoblots and their autoradiographs for three other GATase-specific MAbs designated 4.Al, 21.A8, and 31.All.

H. Immunoaffinity Chromatography.

SDS (0.2%) was added to 1.2 ml of $^3$H-labeled GATase (Fraction 3, 1.5 mg protein). After heating to 80° C. for 10 minutes and cooling, sodium deoxycholate (Sigma Chemical Co.) was added to give a final concentration of about 0.5%. This solution was loaded onto a 1.2 ml column (0.8 cm diameter) packed with MAb 19.2 covalently linked to cyanogen bromide-activated Sepharose 4B, 1.3 mg MAb/ml beads, prepared according to Cuatrecasas (J. Biol. Chem. 245:3059–3065(1970)), equilibrated with buffer containing 20 mM Tris-HCl (pH 8.0), 0.9% NaCl and about 0.5% sodium deoxycholate. The column was then washed with 8 volumes of this buffer yielding the unbound fraction. The bound fraction was eluted with the same buffer containing 4M KSCN.

Initial attempts to precipitate the $^3$H-labeled GATase with one of these MAbs, 19.2, and goat anti-mouse IgG-Sepharose were unsuccessful. However, when the labeled enzyme was first denatured with sodium dodecyl sulfate (SDS), 3.5-fold more radioactivity was precipitated by 19.2 than by the same concentration of non-immune mouse IgG (Table 1, below). Similar results were obtained using MAb 4.A1 (Table 1).

TABLE 1

| MAb | GATase Precipitation (cpm ± S.D.) | MAb:IgG Ratio |
|---|---|---|
| IgG | 180 ± 24 | — |
| 19.2 | 661 ± 49 | 3.7 |
| 4.A1 | 604 ± 56 | 3.4 |

(a) [$^3$H-methyl]GATase (50 μg of Fraction 3 protein) was incubated 2 hours in buffer A with 10 μg MAb 19.2, MAb 4.A1 or non-immune mouse myeloma IgG, in a volume of 0.5 ml. The precipitates that formed upon the addition of Sepharose-linked goat anti-mouse IgG (Sigma), were pelleted and washed three times with buffer A. Bound GATase was released by adding 0.5 ml 2 N NaOH and radioactivity in the supernatant after centrifugation was determined by scintillation counting. Values are the mean and standard deviation of three measurements.

It should be noted that without the addition of sodium deoxycholate to the elution buffer, the purified enzyme was found to stick to the collection vessels. The presence of the low concentration of deoxycholate in the buffer served to maintain the protein in solution for further purification or use.

To further demonstrate the specificity of MAb 19.2 and to evaluate its usefulness for immunoaffinity chromatography, we covalently linked the antibody to CNBr-activated Sepharose 4B (Pharmacia, Sweden). When active GATase was loaded onto a column of this affinity resin, virtually all (99%) of the activity applied was recovered in the unbound fractions that washed through the column. However, when $^3$H-labeled GATase was denatured with SDS before being applied to the column, 60% of the radioactivity was bound. Of this about 10% subsequently could be eluted by 4M KSCN.

It is to be noted that since the immunoaffinity procedure requires the transferase to be denatured, purity of the eluted protein could not be assessed by specific activity of the transferase. Homogeneity is therefore defined herein, as the presence of a single human protein band in SDS-PAGE. Characterization of such protein by amino acid sequence analysis will further confirm its homogeneity.

Figure 4:
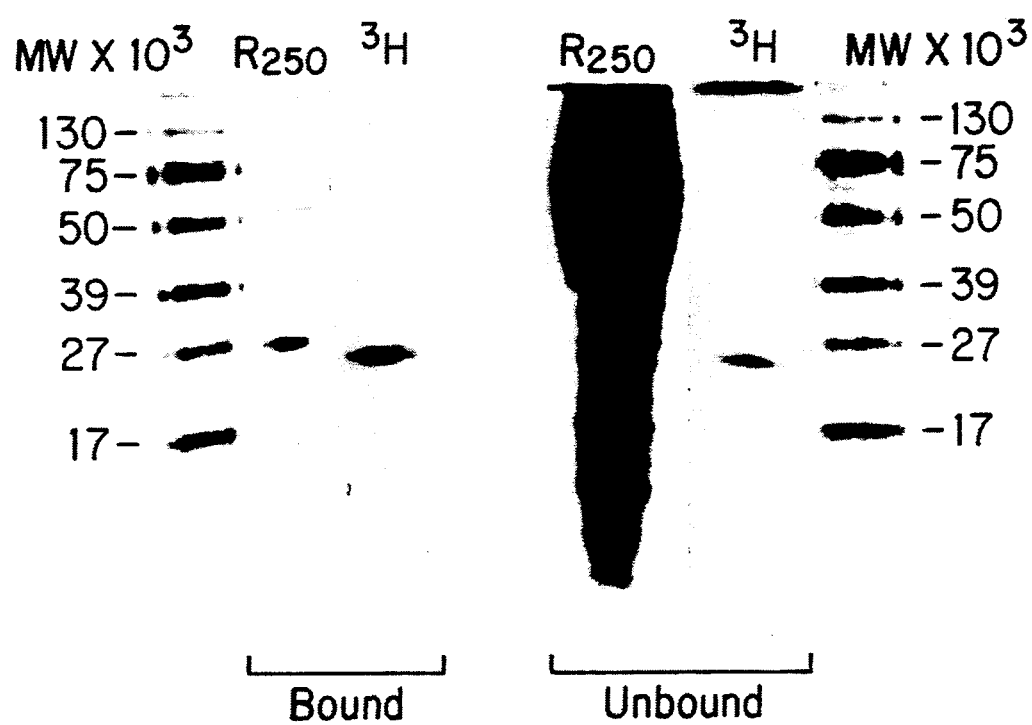
FIG. 4. SDS-PAGE of bound and unbound fractions after immunoaffinity chromatography. The samples were prepared and electrophoresed as described in FIG. 2. After staining with Coomassie brilliant blue R-250, the gel was dried and autoradiographed. Lanes marked "$R_{250}$" are the stained gel. Adjacent lanes labeled "$^3$H" are the corresponding autoradiographs.

SDS-PAGE analysis of the fractions from immunoaffinity chromatography (FIG. 4) indicates that the unbound fraction contained a large amount of protein including a band of $^3$H-labeled GATase at 25-KDa (see corresponding autoradiograph). By contrast, the bound fraction appeared to contain only two polypeptides at 27-KDa and 52-KDa, corresponding to the mouse IgG heavy and light chains that had leached from the column. However, the autoradiograph of this fraction revealed an $^3$H-labeled band at 25-kDa that represents considerably more GATase than that present in the unbound fraction lane. Thus, immobilized 19.2 specifically bound GATase and yielded highly purified enzyme.

Figure 3:
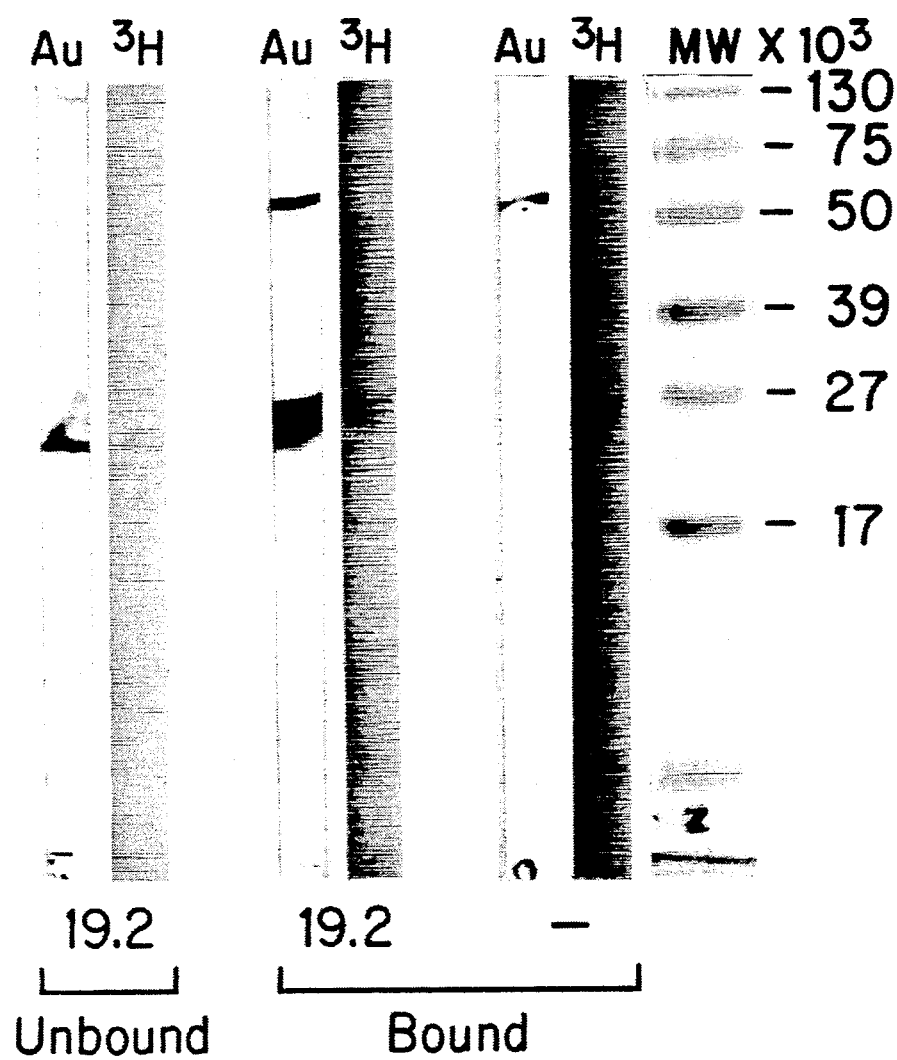
FIG. 3. Immunoblot of the bound and unbound fractions resulting from immunoaffinity chromatography. About 2% of the unbound fraction and 33% of the bound fraction were equilibrated with water and concentrated (using Centricon 10 membranes, Amicon) before SDS-PAGE and transfer to nitrocellulose. Blotted strips were probed with MAb 19.2 and gold labeled secondary antibody prior to autoradiography. A blotted strip of the bound fraction probed with the secondary antibody only, is shown on the right.

Western blot analysis of the bound and unbound fractions from the affinity column confirmed that although much of the GATase passed through, a significant fraction was bound by the column (FIG. 3). In addition to the band at 25-KDa, a second band at 52-KDa in the blot of the bound fraction was also seen. When a duplicate Western blot strip was probed with the secondary antibody only, this band was still present, indicating that it represents mouse IgG heavy chain which had leached from the immunoaffinity column. The exact coincidence of the radiolabeled band in the autoradiograph of these strips with the 25-KDa immunoreactive band in the same strips probed with 19.2 confirms the specificity of this monoclonal antibody.

In summary, we have produced four monoclonal antibodies that are specific for human $O^6$-guanine alkyltransferase. All these antibodies appear to recognize the antigen only after denaturation by SDS. This characteristic suggests that the most antigenic sites on the enzyme may be exposed when the protein unfolds.

Immunoaffinity chromatography with MAbs 19.2 and 4A.1 can be used to obtain highly purified GATase.

We claim:

1. A process for preparing a homogeneous preparation of denatured human $O^6$-guanine alkyltransferase comprising the steps of:
   a) denaturing human $O^6$-guanine alkyltransferase;
   b) contacting said denatured human $O^6$-guanine alkyltransferase resulting from step a) with a monoclonal antibody specific for said denatured human $O^6$-guanine alkyltransferase, which monoclonal antibody is bound to a substrate, so that said denatured human $O^6$-guanine alkyltransferase and said monoclonal antibody form an immunocomplex; and
   c) eluting said denatured human $O^6$-guanine alkyltransferase from said substrate-bound monoclonal antibody so that said homogeneous preparation is obtained.

2. The process of claim 1 further comprising an elution buffer comprising about 0.5% deoxycholate.

3. The process of claim 2, wherein said elution buffer further comprises 4M KSCN.

4. The process of claim 1, wherein said human $O^6$-guanine alkyltransferase is purified about 30,000-fold.

* * * * *